US010076265B2

(12) United States Patent
Dyer et al.

(10) Patent No.: US 10,076,265 B2
(45) Date of Patent: Sep. 18, 2018

(54) MAGNETIC RESONANCE VISIBLE LABELS AND MARKERS FOR ENCODING INFORMATION

(71) Applicant: Synaptive Medical (Barbados) Inc., Bridgetown (BB)

(72) Inventors: Kelly Noel Dyer, Toronto (CA); Jeff Alan Stainsby, Toronto (CA); Fergal Kerins, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 15/328,987

(22) PCT Filed: May 8, 2015

(86) PCT No.: PCT/IB2015/053396
§ 371 (c)(1),
(2) Date: Jan. 25, 2017

(87) PCT Pub. No.: WO2016/181182
PCT Pub. Date: Nov. 17, 2016

(65) Prior Publication Data
US 2017/0209068 A1    Jul. 27, 2017

(51) Int. Cl.
*A61B 5/055* (2006.01)
*A61B 90/96* (2016.01)
(Continued)

(52) U.S. Cl.
CPC .............. *A61B 5/055* (2013.01); *A61B 90/90* (2016.02); *A61B 90/94* (2016.02); *A61B 90/96* (2016.02)

(58) Field of Classification Search
None
See application file for complete search history.

(56) References Cited

U.S. PATENT DOCUMENTS 6,333,970 B1    12/2001  Lemaitre et al.
2006/0138211 A1*  6/2006  Lubow ................... G06K 17/00
                                                    235/375
(Continued)

FOREIGN PATENT DOCUMENTS

WO        2014032171        3/2014
WO    WO 2014181230 A2 *   11/2014   .......... G06F 19/321

OTHER PUBLICATIONS

The International Search Report and Written Opinion dated Aug. 12, 2015 for International Application PCT/IB2015/053396.
(Continued)

*Primary Examiner* — Amanda Lauritzen Moher
*Assistant Examiner* — Farouk Bruce
(74) *Attorney, Agent, or Firm* — Quarles & Brady LLP (57) ABSTRACT

Systems and methods for manufacturing and using magnetic resonance ("MR") visible labels or markers to encode information unique to the subject or object being imaged by a magnetic resonance imaging ("MRI") system are provided. The use of such MR-visible labels or markers enables unique information associated with the subject or object being imaged to be encoded into the images of the subject or object. This information can be used to anonymize protected health information ("PHI"); to provide detailed information about a surgical simulation device, quality assurance phantom, or the like; to provide spatial orientation and registration information; or so on.

4 Claims, 4 Drawing Sheets

(51) Int. Cl.
  *A61B 90/94*     (2016.01)
  *A61B 90/90*     (2016.01)

(56) References Cited

U.S. PATENT DOCUMENTS

| | | | |
|---|---|---|---|
| 2006/0204064 A1* | 9/2006 | Hay | G06K 9/32 |
| | | | 382/128 |
| 2008/0204236 A1* | 8/2008 | Kraft-Oz | G06Q 50/24 |
| | | | 340/572.1 |
| 2009/0177077 A1* | 7/2009 | Piferi | G01R 33/285 |
| | | | 600/414 |
| 2011/0076983 A1 | 3/2011 | Rofougaran | |
| 2012/0302863 A1 | 11/2012 | O'Neill | |
| 2014/0070012 A1* | 3/2014 | Hunt | G06K 19/06037 |
| | | | 235/494 |
| 2015/0223907 A1* | 8/2015 | Kieser | A61B 17/7004 |
| | | | 623/17.16 |

OTHER PUBLICATIONS

The International Preliminary Report on Patentability dated Nov. 18, 2016 for International Application PCT/IB2015/053396.

* cited by examiner

MAGNETIC RESONANCE VISIBLE LABELS AND MARKERS FOR ENCODING INFORMATION

CROSS-REFERENCE TO RELATED APPLICATIONS

This application represents the national stage entry of PCT International Application PCT/IB2015/053396 filed May 8, 2015. The contents of this application are hereby incorporated by reference as if set forth in their entirety herein.

BACKGROUND OF THE INVENTION

The field of the invention is systems and methods for magnetic resonance imaging ("MRI"). More particularly, the invention relates to systems and methods for labeling.

Typical MRI scanning procedures rely on the MRI system operator to input unique identifying characteristics of the subject or object being scanned. This information is then normally encoded into header information of the digital images generated by the scan. In various scenarios, however, this information may not be input, may be input incorrectly, or may need to be subsequently anonymized. Additionally, this identifying information only stays associated with the images as long the images remain in an image format that allows such header information to be associated with the image data, such as with DICOM-format images. If the images are converted to another format, the pertinent information may be lost.

There remains a desire to provide a form of subject or object labeling that does not rely on image header information. For example, when scanning phantom objects (e.g., for quality control purposes, scanner characterization purposes, patient simulations), there is rarely a rigorous identification process analogous to a medical record number for patients. Furthermore, there may be multiple phantoms that all give similar image characteristics and therefore cannot be simply differentiated by their image characteristics. Having some standardized method to identify the object as a phantom, and which phantom in particular, could be beneficial for automated post-processing evaluations or other image quality analysis methods.

Similarly, it would be desirable to have a method of uniquely identifying human subject scans, in addition to personal medical record numbers tagged in the digital header information, which would help resolve issues when patient information is input incorrectly. Such a method would also preferably provide an anonymized reference code compatible with image anonymization procedures.

SUMMARY OF THE INVENTION

The present invention overcomes the aforementioned drawbacks by providing magnetic resonance ("MR")-visible labels or markers that can be used to encode information about an object or subject being imaged into images of that object or subject.

It is an aspect of the invention to provide an MR-visible label that includes a substrate having a first side and a second side. A plurality of indicia are located on the first side of the substrate. These indicia include a surface area having magnetic resonance properties that are different from magnetic resonance properties of the substrate such that the plurality of indicia are capable of being imaged with a magnetic resonance imaging ("MRI") system. The plurality of indicia are arranged in a pattern that encodes information about an object being imaged with the MRI system.

It is another aspect of the invention that the plurality of indicia can be arranged in a pattern that defines a quick response ("QR") code; contains a plurality of line segments that form a unique two-dimensional geometric shape; defines a barcode; contains a plurality of spaced apart beads, dots, or other marks, that represent a binary, tertiary, or other encoding; and so on.

It is another aspect of the invention that the plurality of indicia can be composed of an MR-visible gel, and MR-visible ink, or any other suitable MR-visible material.

It is another aspect of the invention that the plurality of indicia can be formed by removing material from the substrate. For example, material can be removed using laser cutting or die cutting techniques.

It is another aspect of the invention that the information encoded by the plurality of indicia can include protected health information ("PHI") about a subject, or information about a phantom, surgical simulation device, or other medical device, including part numbers, manufacture dates, and expiration dates. The information encoded by the plurality of indicia can also indicate instruction for automatically processing images of the object or subject. The information encoded by the plurality of indicia can also include a unique identifier that is associated with data stored in a database. Such data can include those types of information described above, including PHI; device part numbers, manufacture dates, and expiration dates; or instructions for automatically processing images.

It is another aspect of the invention to provide an MR-visible marker that includes a substrate composed of a first material having first magnetic resonance imaging characteristics. A plurality of indicia are formed in the substrate. The plurality of indicia are composed of a second material having second magnetic resonance imaging characteristics that are different from the first magnetic resonance imaging characteristics. The plurality of indicia are arranged in a pattern that encodes information about an object being imaged with the MRI system.

It is yet another aspect of the invention to provide a magnetic resonance visible marker that includes a substrate composed of a magnetic resonance-visible material. The substrate is arranged as a unique three-dimensional shape that when viewed in a two-dimensional plane through the substrate forms a pattern that encodes information about an object being imaged with the MRI system.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for manufacturing and using magnetic resonance ("MR") visible markers to encode information unique to the subject or object being imaged by an MRI system. As an example, the MR-visible markers can include MR-visible labels or MR-visible three-dimensional objects. The use of such MR-visible markers enables unique identification of the imaged object by simple identification and processing of the MR images in which the marker is visible. By way of example, the object can be a subject or a phantom, such as a quality control or quality assurance phantom.

Generally speaking, the MR-visible markers described here can include any suitably designed MR-visible object that has a unique characteristic that allows it to be identified within typical MR images and that can encode information in numerous unique values. The MR-visible markers are preferably designed with spatially unique borders that allow for proper identification of the orientation of the MR-visible marker in a given MR image because any given MR image could represent the MR-visible marker with any arbitrary rotation or flip.

Figure 1:
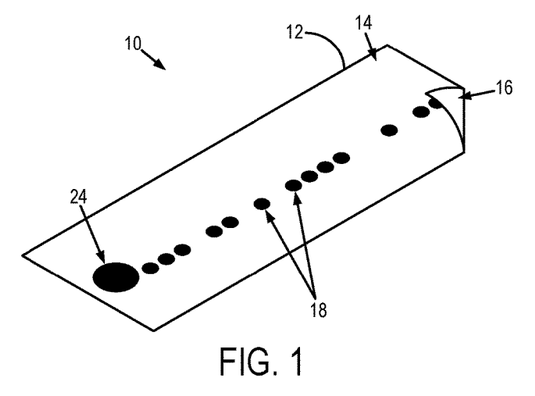
FIG. 1 is an example of a magnetic resonance ("MR")-visible label having formed thereon a plurality of indicia that encode information about an object or subject being imaged, wherein the indicia are arranged to encode the information using a binary encoding.

As mentioned above, in some embodiments the MR-visible markers of the present invention can include MR-visible labels, such as the label 10 illustrated in FIG. 1. As will be described below, in some other embodiments the MR-visible markers can include three-dimensional MR-visible objects.

In general, MR-visible labels 10 can include a substrate 12 having a first side 14 and a second side 16. The substrate 12 generally includes a sheet, and may be composed of a plastic, paper, or other similar material. The first side 14 of the substrate 12 includes a plurality of indicia 18 that are arranged into a pattern that encodes information about an object or subject to be imaged with an MRI system. A number of different examples of how these indicia 18 can be arranged is provided below, as are examples of the types of information that can be encoded in the pattern formed by the indicia 18.

The indicia 18 generally include a surface area having magnetic resonance properties that are different from the magnetic resonance properties of the substrate 12. As one example, the indicia 18 can be composed of a material that has a different longitudinal relaxation time, $T_1$, from the substrate 12. As other examples, the magnetic resonance properties can also include transverse relaxation time, $T_2$; proton density, $\rho$; magnetic susceptibility, $\chi$; or other magnetic resonance properties that can be utilized as the basis for generating an image contrast in an MR image.

In some embodiments, the second side 16 of the substrate 12 can include an adhesive layer for adhering the label to the receiving surface of an object or subject. Where the label 10 includes an adhesive layer, the substrate 12 can be provided on a liner, such as a liner paper. In some configurations, the adhesive layer is configured such that the label 10 can be releasably adhered to an object or subject. In these instances, the adhesive layer can be made from an easily removable adhesive, including removable pressure-sensitive adhesives, rubber-based hot-melt adhesives, and so on.

In some embodiments, the MR-visible label 10 includes indicia 18 formed using MR-visible inks, gels, or other materials that are deposited or otherwise coupled to the first side 14 of the substrate 12. One example of another material that is MR-visible and can be used to form indicia 18 is toothpaste, which can be printed or otherwise deposited on the substrate 12.

In general, the choice of MR-visible material from which the indicia 18 will be formed will be influenced by the complexity of the pattern in which the indicia 18 will be, the relative signal generated by the MR-visible material, and the spatial resolution necessary to resolve the detail in the pattern of indicia 18. For instance, when using MR-visible inks, a sufficient thickness of ink should be used to generate enough signal for the pattern of indicia 18 to be reliably imaged.

Figure 2A:
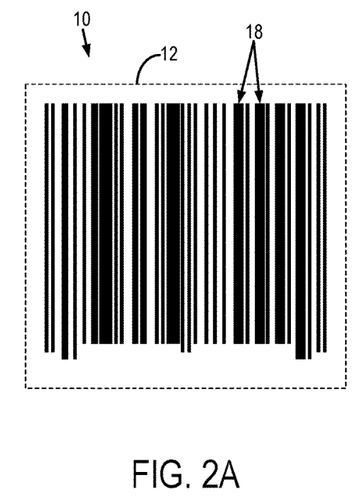
FIG. 2A is an example of an MR-visible label in which the plurality of indicia are formed as a barcode.
Figure 2B:
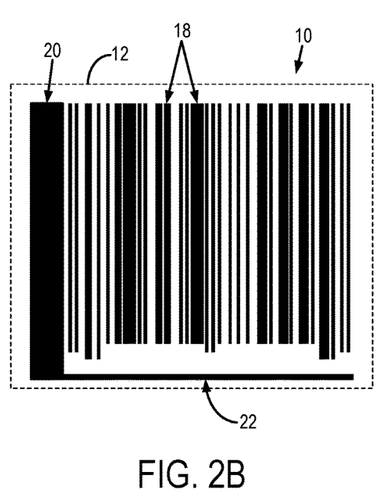
FIG. 2B is an example of an MR-visible label in which the plurality of indicia are formed as a barcode having additional indicia that provide spatial orientation information about the label.

Referring now to FIGS. 2A and 2B, as one example, the indicia 18 can be arranged in a pattern that includes a plurality of line segments that are separated in space to create a barcode label. In these configurations, the barcode label can implement a universal product code ("UPC") barcode symbology; however, other barcode symbologies could also be readily implemented. Such indicia 18 can be created by printing the desired pattern on the substrate 12 of the label 10 using MR-visible inks, gels, or other materials. In other examples, such indicia 18 can be created by arranging thin strips of MR-visible material into the desired pattern. In these examples, the MR-visible material can include a material containing proton signals with short longitudinal relaxation time and moderate-to-long transverse relaxation time properties. For instance, the MR-visible material could include small tubes containing water doped with MR-visible material, such as vitamin E, gadolinium, iron oxide particles, or so on.

As illustrated in FIG. 2B, the barcode pattern can be augmented with additional lines that provide unique spatial orientation information, such as the thick bar 20 on the left of the barcode and the thin bar 22 running underneath the barcode.

Figure 3:
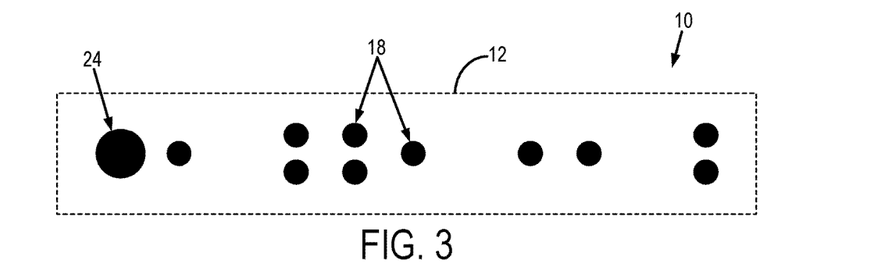
FIG. 3 is an example of an MR-visible label in which the plurality of indicia are arranged to encode information using a tertiary encoding.

As another example, the indicia 18 can be arranged in a pattern that includes a simple line of visible markers, such as those illustrated in FIG. 1. In these configurations, the indicia 18 can be arranged in a pattern that encodes information using a binary encoding. For example, the visible markers can be separated in space using a fixed spacing such that the presence or absence of a marker at a particular location can be respectively encoded as a binary value of "1" or "0." It will be appreciated that other encodings could be similarly implemented in this manner. As one example, illustrated in FIG. 3, a tertiary encoding could also be implemented. For a tertiary encoding, a linear pattern of zero, one, or two markers at fixed spacing can be used to encode values of "0," "1," or "2," respectively.

Referring again to FIG. 1, a linear pattern of indicia 18 can be augmented to include a visible, well-defined start location that not only indicates the beginning of the pattern, but provides unique spatial orientation information. As one example, such as the one illustrated in FIG. 1, this additional marker 24 can simply be a larger-sized marker; however, in other configurations the additional marker 24 could be uniquely shaped, or so on.

Figure 4:
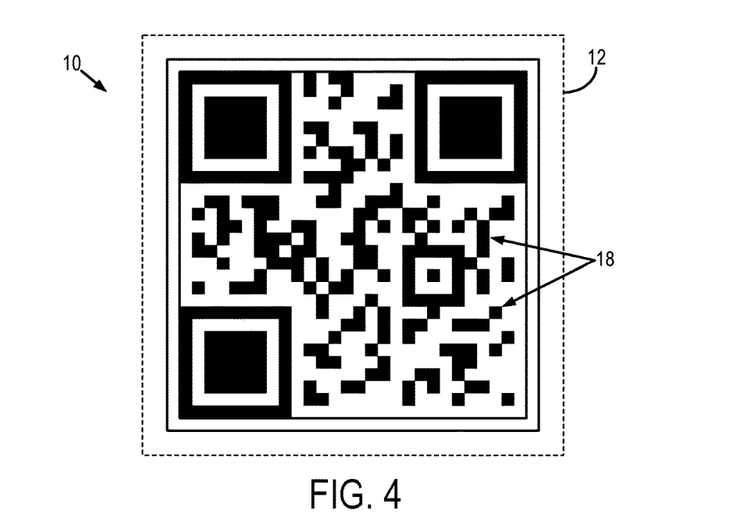
FIG. 4 is an example of an MR-visible label in which the plurality of indicia are formed as a quick response ("QR") code.

As another example, the indicia 18 can be arranged in a two-dimensional pattern that uniquely encodes information. For instance, the indicia 18 could be arranged as a quick response ("QR") code, as illustrated in FIG. 4. Such pattern of indicia 18 could be created by printing the desired pattern on the substrate 12 of the label 10 using MR-visible inks, gels, or other materials. Using two-dimensional patterns of indicia 18 has the benefit that more complex information can be encoded in a smaller label 10. Robust spatial orientation information can also be encoded in a QR code. As will be described below, this spatial orientation information can be used not only to identify the orientation of the subject within the field-of-view, but also to allow robust co-registration of images in which the label 10 is present. In some embodiments, the label 10 can serve as a target for co-registration, such that the pattern of indicia 18 aids in the co-registration process, such as through proper alignment of the pattern of indicia 18 in multiple different images.

Figure 5:
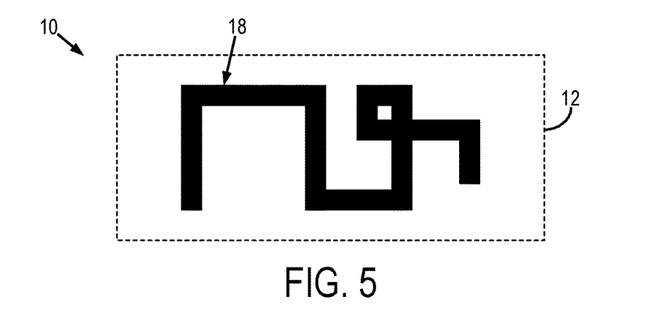
FIG. 5 is an example of an MR-visible label in which the plurality of indicia are formed as a unique two-dimensional geometric shape that, in this example, is arranged as a plurality of line segments.

In other configurations, the indicia 18 could be arranged as a one-dimensional or two-dimensional geometric pattern that is designed to be unique. One example of such a configuration is illustrated in FIG. 5, whereby a plurality of line segments are ordered to form a unique two-dimensional geometric pattern, or symbol, that can be used to encode information. In such configurations, the line segments can have a fixed length or a variable length.

In these foregoing examples, the indicia 18 can be created by printing the desired pattern on the substrate 12 of the label 10 using MR-visible inks, gels, or other materials. In other examples, the indicia 18 can include MR-visible beads or other markers that are coupled to the first side 14 of the substrate 12. As one example, the beads or other markers could include vitamin E tablets.

Figure 6:
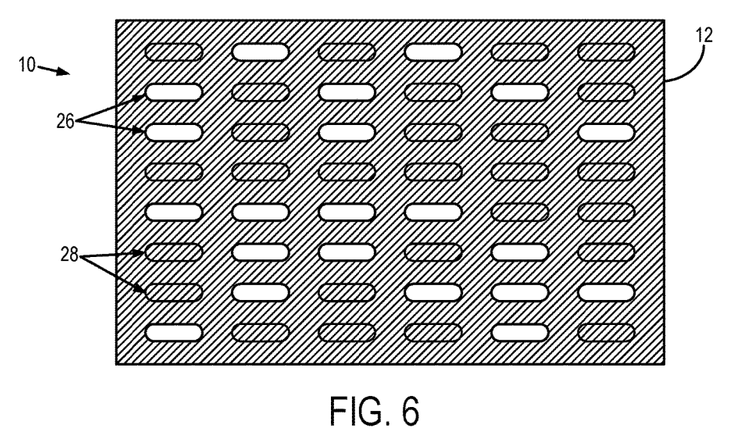
FIG. 6 is an example of an MR-visible label in which the plurality of indicia are formed as holes left when removing perforated regions of the label.

In some other embodiments, however, the indicia 18 can be formed by removing material from the substrate 12. As one example, the substrate 12 can be composed of an MR-visible material and can be manufactured to allow the simple removal of regions 26 from the substrate 12. For instance, regions 26 in the substrate 12 could be manufactured as perforated regions 28 that can be manually removed, or removed by the aid of an automated tool that punches out a pattern of these perforated regions 28 to form a pattern of indicia 18 in the substrate 12. An example of such a "punch-card" type of label 10 is illustrated in FIG. 6, wherein the indicia 18 can be formed by removing perforated regions 28 from the substrate 12.

As another example of indicia 18 that can be formed by removing material from the substrate 12, the substrate 12 can be composed of foil-backed paper. In this example, indicia 18 can be formed in the substrate 12 by cutting a pattern in the foil-backed paper. As one example, the foil-backed paper can be laser cut. As another example, the foil-backed paper can be cut using a machine, such as a printing press that has insertable die blocks. In this manner, the die blocks can be used to cut out shapes in a piece of foil-backed paper. A challenge with constructing the label 10 from foil-backed paper, however, is that the susceptibility artifacts generated by the foil may mean that the signal generating portions of the label could be partially obscured.

As mentioned above, in some embodiments, the MR-visible markers of the present invention can include three-dimensional MR-visible objects that are manufactured to contain a plurality of indicia that form a pattern that encodes information. In some embodiments, the plurality of indicia can be formed as a plurality of joined lined segments or shapes that together create a single geometric shape.

Three-dimensional MR-visible markers have the added benefit that they can be imaged in different imaging planes without moving the marker, thereby allowing images to be acquired in different orientations while still providing a marker that encodes information and is visible in the image. Markers can be arranged such that the same information is encoded when viewing the marker from different directions or, alternatively, such that different information is encoded when viewing the marker from different directions. As one example of the latter instances, different information can be encoded when viewing the marker in the axial plane, the coronal plane, or the sagittal plane. This differential encoding of information can be used, for example, to readily identify the plane through which the subject or object has been imaged.

Figure 7A:
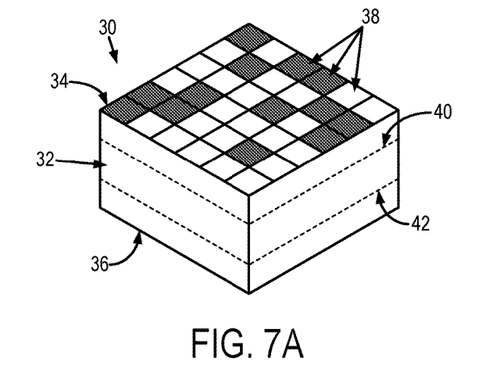
FIG. 7A is an example of a three-dimensional MR-visible marker having formed thereon a plurality of indicia that encode information about an object or subject being imaged.

One example of a three-dimensional MR-visible marker is illustrated in FIG. 7A. In general, such markers 30 can include a substrate 32 that extends from a first side 34 of the marker 30 to a second side 36 of the marker 30. A plurality of indicia 38 are then formed in the marker 30 such that the indicia 38 can be imaged using MRI and are arranged in a pattern or other manner such that information can be encoded by the indicia 38.

In some embodiments, the indicia 38 can include channels, wells, apertures, and so on that are formed in the substrate 32 and then filled with an MR-visible material. As one example, such indicia 38 can be filled with an MR-visible fluid, such as water doped with gadolinium, vitamin E, iron oxide particles, or another MR-visible material. In some other embodiments, the indicia 38 formed as channels, wells, apertures, and so on, can be left empty and the substrate 32 can be composed of an MR-visible material. In this manner, the substrate 32 will be visible in magnetic resonance images and the absence of signal caused by the indicia 38 will depict a pattern that can encode the desired information. It will be appreciated by those skilled in the art that the desired information can also be suitably encoded by the pattern associated with the depiction of the substrate 32 in the MR image. It will also be appreciated, then, that in some embodiments both the substrate 32 and the indicia 38 can be configured to form first and second patterns that both encode information.

Figure 7B:
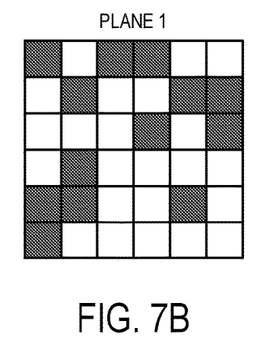
FIG. 7B is an example of an axial plane through the MR-visible marker of FIG. 7A illustrating a first pattern of indicia in the marker.
Figure 7C:
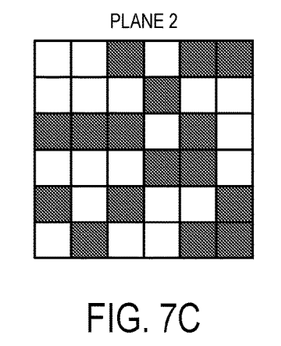
FIG. 7C is an example of another axial plane through the MR-visible marker of FIG. 7A illustrating a second pattern of indicia in the marker.
Figure 8:
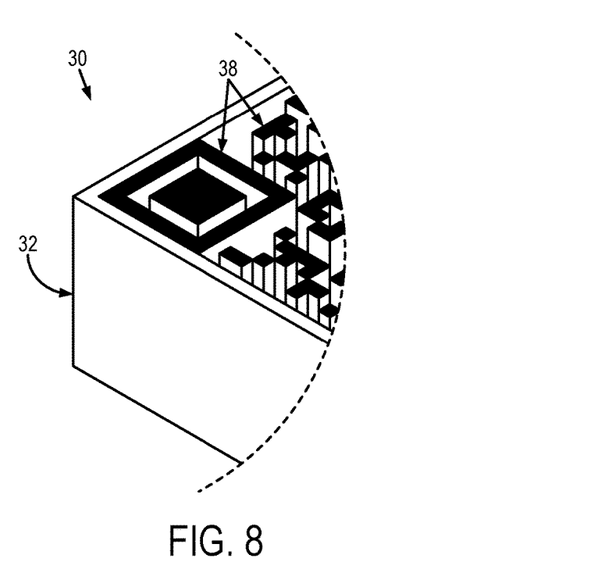
FIG. 8 is an example of a three-dimensional MR-visible marker in which the plurality of indicia are formed as a QR code when the marker is viewed through an axial plane.

The indicia 38 described above can be arranged such that the same pattern exists throughout the marker 30. Alternatively, as illustrated in FIGS. 7B and 7C, the indicia 38 can be arranged throughout the marker 30 such that different patterns are formed in different planes through the marker 30. For example, the pattern formed by the indicia 38 in a first plane 40 and be different from the pattern formed by the indicia 38 in a different, second plane. This configuration can be useful to encode different information in different image slices through the same subject or object. As one example, phantoms may have different properties or characteristics at different regions within the phantom. When imaging such a phantom, it can be useful to have information pertaining to these different regions encoded in the images of those regions. Using a suitably designed three-dimensional MR-visible marker, such differential information can be encoded across different slices in the imaging volume. When imaging a phantom that has different properties at different locations throughout the phantom, it can be useful to encode different information pertaining to those regions Like the MR-visible labels, the pattern of indicia 38 in the three-dimensional MV-visible markers 30 can be formed to encode information through numeric encoding (e.g., binary, tertiary), three-dimensional barcodes, three-dimensional QR codes, and so on. One example of a three-dimensional MR-visible marker 30 whose cross-section forms a QR-code is illustrated in FIG. 8.

Figure 9A:
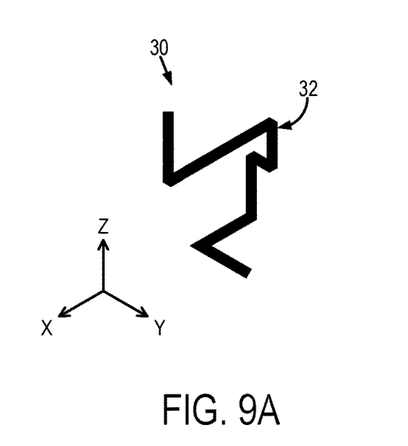
FIG. 9A is an example of a three-dimensional MR-visible marker formed as a unique three-dimensional shape that, in this example, is arranged as a plurality of linear segments.

In other examples, the three-dimensional visible marker 30 can be constructed from a substrate 32 that is shaped in a unique, three-dimensional geometric shape, as illustrated in FIG. 9A. Such markers can be constructed using 3D printing or other suitable techniques. These markers can be composed of MR-visible materials such that they can be readily imaged using MRI. In some embodiments, markers 30 that are constructed as unique three-dimensional shapes can be made solid or hollow. For the latter configuration, the marker 30 can be filled with an MR-visible material or, alternatively, left empty while the marker 30 itself if formed from an MR-visible material.

Figure 9B:
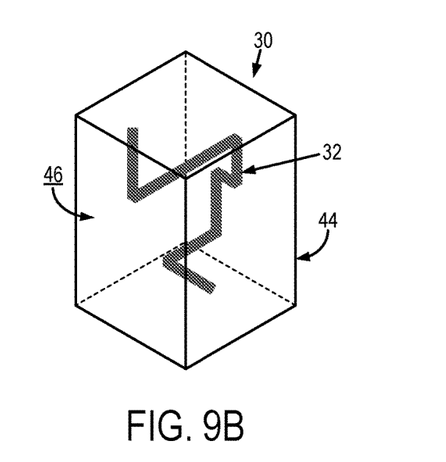
FIG. 9B is an example of a three-dimensional MR-visible marker formed as a unique three-dimensional shape that is placed in a container that contains an MR-visible medium, such as an MR-visible fluid.

As illustrated in FIG. 9B, in some other embodiments, the markers can be placed in a container 44 that contains an MR-visible medium 46, such as water doped with an MR-visible material. In these embodiments, the MR-visible marker 30 is composed of a material having magnetic resonance properties sufficiently different from the MR-visible medium 46, such that a sufficient image contrast exists between the marker 30 and the medium 46.

Having described a number of different examples of MR-visible labels and markers, a discussion of the different types of information that can be encoded in such labels and markers is now provided.

The amount of information that can be encoded in a given MR-visible label or marker will depend on the pattern of indicia 18 used. For example, a barcode may be capable of encoding only twenty digits, whereas a QR code may be capable of encoding several thousand characters.

As such, patterns of indicia 18 that can encode fewer bits or characters are preferably used to encode smaller pieces of information that can then be related to more information that is stored in a separate storage device. For example, a barcode could be used to encode a unique identifier that is associated with an offline data storage containing a cache of information that may include protected health information, information otherwise stored in a DICOM header, and so on. Similarly, a barcode could be used to encode a part number for a phantom, implanted medical device, or so on.

Patterns of indicia 18 that are capable of encoding larger amount of information can similarly encode a unique identifier that is linked to a separate data storage, or can be used to encode a limited set of information about the subject or object being imaged. For example, a QR code may be capable of storing sufficient protected health information or, in the instance of an imaging phantom, may be capable of storing sufficient information about the phantom.

Examples of information about a phantom that can be encoded in an MR-visible label or marker include part numbers, a description of the phantom type, the type of material(s) used in the phantom, manufacture dates, expiration dates, and so on. When a phantom is used for quality assurance or control, it may be important to know that the phantom has not degraded to a point where it is no longer reliable for quality assurance or control purposes. In this manner, it can be useful to encode manufacture dates, expiration dates, or both for phantoms that will degrade or otherwise change in a known way. Using this information, a phantom—or parts thereof—can be flagged as no longer being reliable when they have passed the encoded expiration date. In some embodiments, the materials used in the construction of the MR-visible label or marker can degrade in a known way, such that the degradation of the label or marker can be associated with the degradation or expiration of the phantom.

Other examples of information about a phantom that can be encoded include unique marker(s) that indicate the images contain phantom data, such that automated post-processing methods can interpret the unique marker to process or identify the images in a particular manner. The encoded information could also differentiate the source of the data (e.g., the exact phantom that was imaged) from phantom image sets that otherwise have an identical—or very similar—image appearance.

Advantageously, the MR-visible labels and markers described here can be used to encode unique identifiers for subjects being imaged in a clinical, or other, setting. As a result, confidential protected health information (e.g., medical record number, date of birth) does not need to be present in the image. By removing this personal information from the medical images, an additional level of security can be provided, further protecting sensitive protected health information.

The MR-visible labels or markers described here could also be constructed as a part of, inserted into, or otherwise coupled to, a simulation device or phantom, such as a poly(vinyl alcohol) (PVA) brain simulator/diffusion phantom. By using PVA formulations of varying density and an array of square or hexagonal wells with narrow walls that could be filled according to a desired QR code or geometric pattern, a unique $T_1$-visible or $T_2$-visible image set could be obtained for a given simulator or phantom. PVA formulations can also be doped with MR visible agents such as micro and sub-microsized particles containing iron or copper to modulate the MR signal. Stable polymeric dispersions in the PVA formulation could also be used with as precursor to a PVA hydrogel using a polymeric component containing an MR visible agent such as Vitamin E.

In some embodiments, the MR-visible label or marker and be incorporated into a phantom or medical device itself. For instance, the substrate 12 can be formed in the phantom (or other medical device) and the plurality of indicia 18 formed, such as by an etching in the substrate 12.

As mentioned above, in addition to encoding pertinent information, the MR-visible labels or markers can also be used for identifying spatial points of reference in an image or for image registration and segmentation purposes. For example, an MR-visible label or marker that contains spatial localization information, spatial orientation information, or both, can be coupled to a subject or object being imaged, such that the depiction of the MR-visible label or marker in the acquired images can be used to facilitate registration, segmentation, or other processing of the images. In some instances, the MR-visible label or marker can be directly affixed to the subject being imaged.

In some instances, such as where MRI is used for surgical planning or radiation treatment planning, the MR-visible label or marker can be coupled to a patient fixation device, thereby establishing a known position on the patient fixation device. The MR-visible label or marker can then be used to positively establish the patient's location within the MRI system. If there is a previously established registration between the fixation device and previous images of the subject, the associated registration could be used to automatically direct the MRI system to image the subject at an already-segmented area of interest.

In some embodiments, the MR-visible label or marker includes indicia 18 formed using a material that can be preferentially imaged using a delta relaxation enhanced magnetic resonance ("DREMR") acquisition. In general, a DREMR acquisition includes field-cycled relaxometry, or field-cycled imaging. The DREMR acquisition is an MRI technique that relies on using underlying tissue contrast mechanisms that vary with the strength of the applied magnetic field in order to generate unique image contrasts. To achieve DREMR contrast, the main magnetic field is varied as a function of time during specific portions of a pulse sequence. As one example, a field-shifting electromagnet coil can be used to perform this field variation.

The DREMR method exploits the difference in the $T_1$ dispersion property (i.e., the variation of $T_1$ with field strength) of targeted $T_1$ contrast agents in bound and unbound states. In particular, this difference is exploited to obtain an image that contains signal only from the contrast agent that is in the bound state, while suppressing signal from the contrast agent in the unbound state.

One example of a contrast agent material that can be preferentially imaged using a DREMR acquisition is iron oxide. The $T_1$ relaxation time of iron oxide based contrast agents vary with the strength of the magnetic field. Therefore, the DREMR method can be used in order to obtain images that contain signal specifically where iron oxide-based contrast agents have accumulated.

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance visible label, comprising: a substrate having a first side and a second side; a plurality of indicia located on the first side of the substrate, the indicia comprising a surface area having magnetic resonance properties that are different from magnetic resonance properties of the substrate such that the plurality of indicia are capable of being imaged with a magnetic resonance imaging (MRI) system; and wherein the plurality of indicia are arranged in a pattern such that the pattern encodes information about an object being imaged with the MRI system; and wherein the plurality of indicia include at least one of a plurality of beads or a plurality of dots that are spaced apart using a spacing that represents a binary encoding of information; wherein the information encoded by the plurality of indicia when arranged in the pattern includes spatial orientation information that defines a spatial orientation of the magnetic resonance visible label; and wherein the encoded information also indicates instructions for automatically processing images of the object; wherein the instructions for automatically processing images of the object include instructions for co-registering the images using the spatial orientation information encoded by the plurality of indicia.

2. The magnetic resonance visible label as recited in claim 1, wherein the object is a subject and the plurality of indicia are arranged in a pattern that also encodes protected health information.

3. The magnetic resonance visible label as recited in claim 1, wherein the object is a phantom and the plurality of indicia are arranged in a pattern that also encodes information about the phantom.

4. The magnetic resonance visible label as recited in claim 1, wherein the encoded information also includes a unique identifier that is associated with data stored in a database.

\* \* \* \* \*